United States Patent
Meyer

(10) Patent No.: US 10,895,414 B2
(45) Date of Patent: Jan. 19, 2021

(54) DRAWER ASSEMBLY FOR A LABORATORY INSTRUMENT

(71) Applicant: Roche Diagnostics Operations, Inc., Indianapolis, IN (US)

(72) Inventor: Thomas Meyer, Walchwil (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 309 days.

(21) Appl. No.: 15/947,929

(22) Filed: Apr. 9, 2018

(65) Prior Publication Data
US 2018/0292126 A1    Oct. 11, 2018

(30) Foreign Application Priority Data

Apr. 10, 2017 (EP) .................................... 17165689

(51) Int. Cl.
*F25D 25/02* (2006.01)
*F25D 31/00* (2006.01)
(Continued)

(52) U.S. Cl.
CPC ......... *F25D 25/025* (2013.01); *F25D 31/006* (2013.01); *G01N 35/04* (2013.01);
(Continued)

(58) Field of Classification Search
CPC ..... F25D 25/025; F25D 31/006; G01N 35/04; G01N 1/31; G01N 2001/305; G01N 35/00;
(Continued)

(56) References Cited

U.S. PATENT DOCUMENTS 7,513,582 B2 * 4/2009 Yoon .................... A47B 88/467
312/319.1
8,439,459 B2 * 5/2013 Johnson .................. E05B 65/46
312/333

(Continued)

FOREIGN PATENT DOCUMENTS

DE   102011003366 A1   8/2012
WO   1993/024234 A2   12/1993

OTHER PUBLICATIONS

European Search Report dated Oct. 30, 2017 in Application No. 17165689.5, 8 pages.

*Primary Examiner* — Benjamin R Whatley
*Assistant Examiner* — Curtis A Thompson
(74) *Attorney, Agent, or Firm* — Roche Diagnostics Operations, Inc.

(57) ABSTRACT

A drawer assembly for a laboratory instrument comprises a drawer loaded with a magazine. The drawer assembly comprises a frame comprising a portion adjacent the drawer that extends in a longitudinal direction. The drawer moves relative to the frame between a retracted position and an extended position. The frame comprises a path having a first portion and a second portion below the first portion. The drawer assembly comprises a rolling element moveable in the path and a lifting mechanism to lift the rolling element from a second portion to a first portion when the drawer is in the retracted position. The path is configured such that the rolling element is located in the first portion and contacts the drawer when the drawer is moved from the retracted position to the extended position and that the rolling element enters the second portion exclusively when the drawer is in the extended position.

14 Claims, 8 Drawing Sheets

(51) Int. Cl.
  *G01N 35/04* (2006.01)
  *G01N 35/00* (2006.01)
  *C12M 1/00* (2006.01)
  *B01L 7/02* (2006.01)
  *G01N 1/31* (2006.01)
  *G01N 1/30* (2006.01)
  *G01N 1/00* (2006.01)
  *A61B 10/00* (2006.01)
  *G01N 1/28* (2006.01)
  *G02B 21/34* (2006.01)

(52) U.S. Cl.
  CPC ............... *A61B 10/00* (2013.01); *B01L 7/02* (2013.01); *C12M 1/00* (2013.01); *G01N 1/00* (2013.01); *G01N 1/28* (2013.01); *G01N 1/30* (2013.01); *G01N 1/31* (2013.01); *G01N 35/00* (2013.01); *G01N 2001/305* (2013.01); *G01N 2001/315* (2013.01); *G01N 2035/00306* (2013.01); *G01N 2035/0418* (2013.01); *G01N 2035/0498* (2013.01); *G02B 21/34* (2013.01)

(58) Field of Classification Search
  CPC ...... G01N 1/00; G01N 1/30; G01N 2001/315; G01N 1/28; G01N 2035/0418; G01N 2035/0498; G01N 2035/00306; C12M 1/00; B01L 7/02; B01L 9/00; B01L 9/06; A61B 10/00; G02B 21/34
  See application file for complete search history.

(56) References Cited

U.S. PATENT DOCUMENTS

2003/0215357 A1* 11/2003 Malterer .............. G01N 35/028
                                                            422/50
2004/0100166 A1*  5/2004 Hoffman ............... E05B 65/466
                                                            312/219
2010/0045153 A1   2/2010 Ritter
2016/0032358 A1*  2/2016 Buse ...................... C12Q 1/686
                                                            435/6.12

* cited by examiner

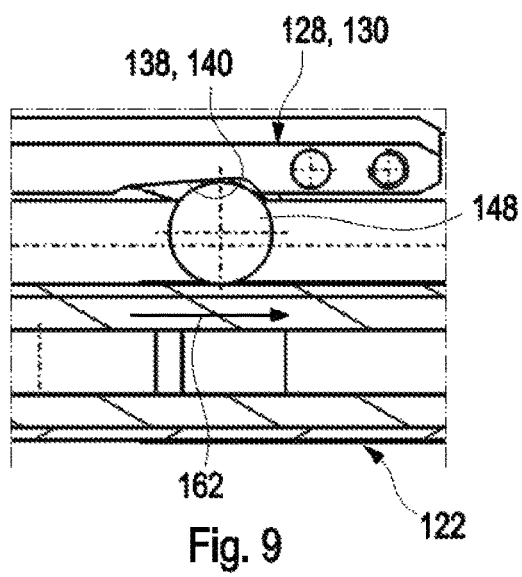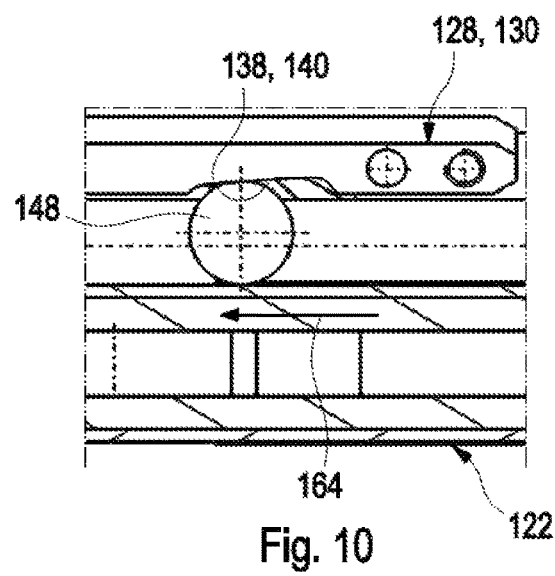
Fig. 9 Fig. 10
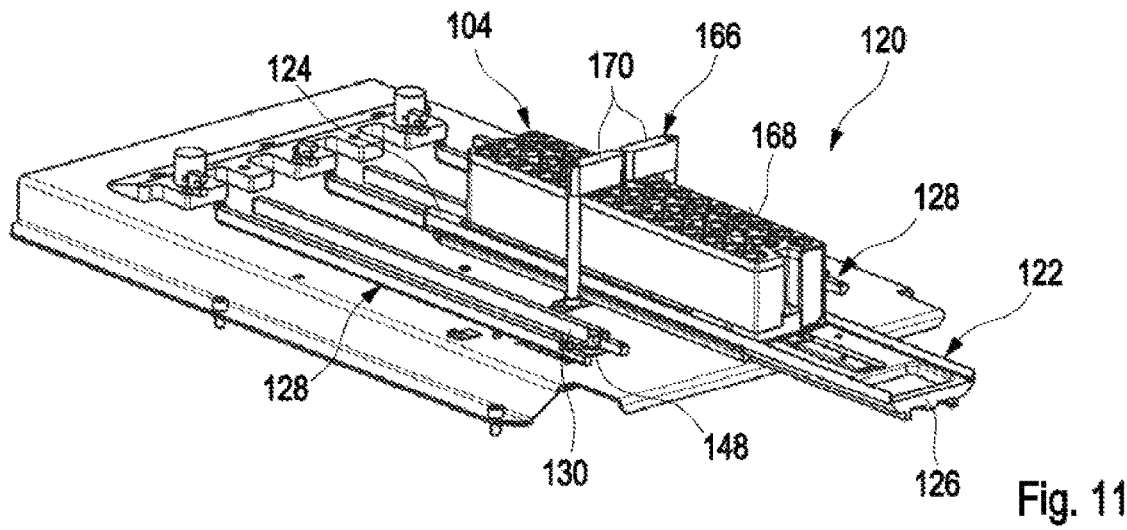
Fig. 11
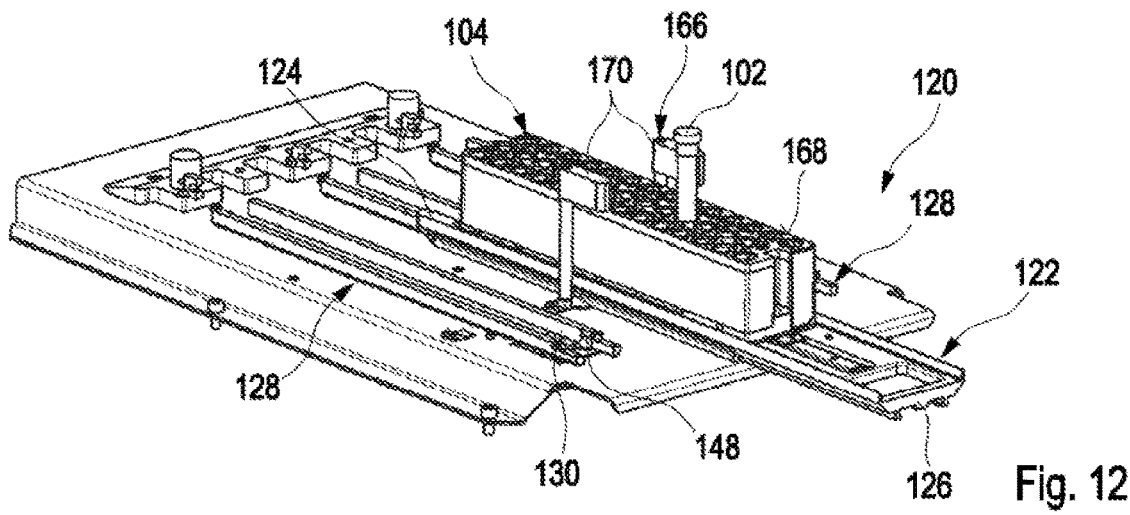
Fig. 12

DRAWER ASSEMBLY FOR A LABORATORY INSTRUMENT

CROSS-REFERENCE TO RELATED APPLICATIONS

This application is based on and claims the benefit of EP 17165689.5 filed Apr. 10, 2017, which is hereby incorporated by reference.

BACKGROUND

The present disclosure relates to a drawer assembly for a laboratory instrument.

In laboratories, such as for example clinical laboratories in which patient samples are examined and submitted to various in-vitro diagnosis tests, test tubes containing samples such as blood, urine, etc. have to be handled in high number and in a cautious but still efficient manner. For years now, automated procedures with corresponding systems and devices have been used in this context.

One aspect during the handling of these sample tubes relates to the tubes being placed in a storage compartment, which can be, for example, a refrigerating device. For efficient handling purposes, the tubes are not handled individually but placed in so-called racks. Usually, the tubes are placed in the racks already by the client, i.e. the person, the department or the institution sending samples to the laboratory, and are then sent or transported to the laboratory in these racks. In the laboratory, the racks with the tubes are subject to further handling steps for testing. Very often, such racks contain tubes with different sizes, heights, diameters, contents, expiration dates of the samples etc., which complicates automated handling so that in some cases further automated insertion of the racks in the test process in the laboratory is not possible, the racks having to be discharged manually.

A laboratory storage and retrieval system to store laboratory sample tubes and retrieve stored sample tubes and a method to handle laboratory sample tubes in a laboratory storage and retrieval system are known. Such systems are part of a so-called storage retrieval module that comprises a rack handler section and a storage section. The rack handler section comprises drawers through which emptied primary racks and/or primary racks containing sample tubes with error designations and/or racks containing at least one retrieved sample tube can be taken out of the storage retrieval module.

Despite the advantages provided by the latter automated sample testing system, there is still room for improvement. With such an automated sample handling system, it is desired to provide an exception out possibility because such an exception out allows either the incoming tubes from a lab transport system or stored tubes to be transported to a so called exception out place. This action is triggered by software command from middleware. The user is then able to manually unload storage racks with "exception out" flagged tubes. Such an exception out possibility may be realized by a drawer. Such a drawer requires some safety provisions in order to ensure that the drawer may be retracted with full or empty racks but may not be re-inserted if not full retracted beforehand. The reason is that the controller of the robotics used for handling the tubes assumes an empty rack when the drawer has been retracted. If there are still any tubes in the racks, the robotics may not detect the same and might collide therewith.

Therefore, there is a need for a drawer assembly for a laboratory instrument and a laboratory instrument having such a drawer assembly that prevent misuse and forces a user to pull the drawer completely out until pushing drawer back into instrument is allowed as well as a need for loading of storage racks with one or more sample tubes in to be mechanically prevented such that the rack needs to be completely empty for re-loading of the drawer.

SUMMARY

According to the present disclosure, a drawer assembly for a laboratory instrument is presented. The drawer assembly can comprise a drawer configured to be loaded with a magazine for receiving vessels for liquids of the laboratory instrument. The drawer can comprise a front end and a rear end. The drawer assembly can also comprise a frame comprising at least one portion arranged adjacent the drawer. The portion can extend in a longitudinal direction from a first end to a second end. The drawer can be moveable relative to the frame between a retracted position, in which the drawer is retracted in the frame and the front end is adjacent the first end, and an extended position, in which the drawer is extended from the frame and the front end is adjacent the second end. The frame can comprise a path having a first portion and a second portion below the first portion. The first portion and the second portion can extend in a direction parallel to the longitudinal direction. The first portion can be tapered towards the first end and facing the drawer. The drawer assembly can also comprise a rolling element moveable in the path and a lifting mechanism configured to lift the rolling element from the second portion to the first portion when the drawer is in the retracted position. The path can be configured such that the rolling element is located in the first portion and contacts the drawer when the drawer is moved from the retracted position to the extended position and that the rolling element is allowed to enter the second portion exclusively when the drawer is in the extended position.

Accordingly, it is a feature of the embodiments of the present disclosure to provide for a drawer assembly for a laboratory instrument and a laboratory instrument having such a drawer assembly that prevent misuse and forces a user to pull the drawer completely out until pushing drawer back into instrument is allowed as well as provide for loading of storage racks with one or more sample tubes in to be mechanically prevented such that the rack needs to be completely empty for re-loading of the drawer. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 9 illustrates a plan view of the portion according to an embodiment of the present disclosure.

FIG. 10 illustrates another plan view of the portion according to an embodiment of the present disclosure.

FIG. 11 illustrates a perspective view of the drawer assembly according to an embodiment of the present disclosure.

FIG. 12 illustrates another perspective view of the drawer assembly according to an embodiment of the present disclosure.

DETAILED DESCRIPTION

Figure 1:
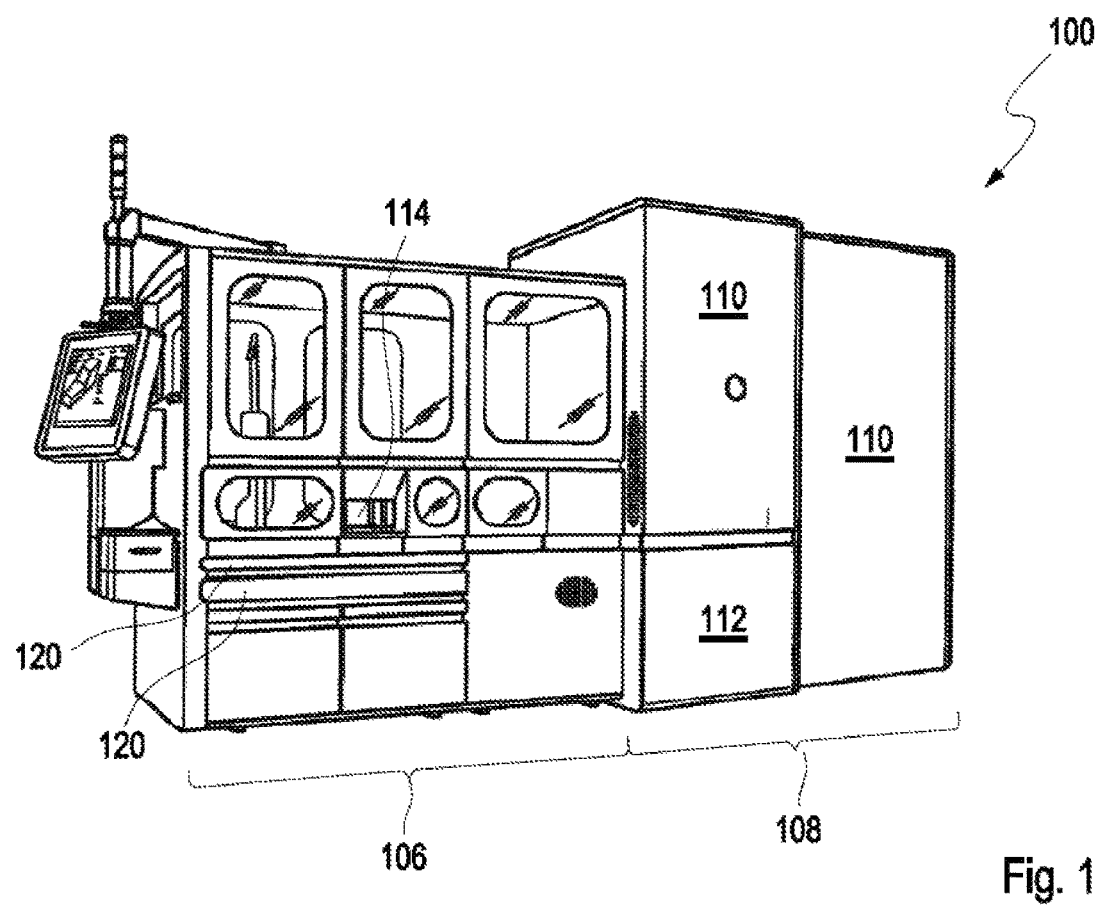
FIG. 1 illustrates a perspective view of a laboratory instrument according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used in the following, the terms "have", "comprise" or "include" or any arbitrary grammatical variations thereof can be used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may all refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "particularly", "more particularly", "specifically", "more specifically" or similar terms can be used in conjunction with optional features, without restricting alternative possibilities. Thus, features introduced by these terms can be optional features and may not be intended to restrict the scope of the claims in any way. The present disclosure may, as the skilled person will recognize, be performed by using alternative features. Similarly, features introduced by "in an embodiment" or similar expressions are intended to be optional features, without any restriction regarding alternative embodiments, without any restrictions regarding the scope of the present disclosure and without any restriction regarding the possibility of combining the features introduced in such way with other optional or non-optional features.

The disclosed drawer assembly for a laboratory instrument can comprise a drawer configured to be loaded with a magazine for receiving vessels for liquids such as, for example, sample tubes, of the laboratory instrument. The drawer can comprise. a front end and a rear end. The drawer assembly can also comprise a frame comprising at least one portion arranged adjacent the drawer. The portion can extend in a longitudinal direction from a first end to a second end. The drawer can be moveable relative to the frame between a retracted position, in which the drawer is retracted in the frame and the front end is adjacent the first end, and an extended position, in which the drawer is extended from the frame and the front end is adjacent the second end. The frame can comprise a path having a first portion and a second portion below the first portion. The first portion and the second portion can extend in a direction parallel to the longitudinal direction. The first portion can be tapered towards the first end and facing the drawer. The drawer assembly can further comprise a rolling element moveable in the path, and a lifting mechanism configured to lift the rolling element from the second portion to the first portion when the drawer is in the retracted position. The path can be configured such that the rolling element can be located in the first portion and can contact the drawer when the drawer is moved from the retracted position to the extended position and that the rolling element can be allowed to enter the second portion exclusively when the drawer is in the extended position.

The term "drawer" as used herein can refer to a box-shaped or flat container that can fit into a piece of a body or casing in such a way that it can be drawn out horizontally to reach its contents.

The term "laboratory instrument" as used herein can refer to any apparatus or apparatus component operable to execute one or more processing steps/workflow steps on one or more biological samples and/or one or more reagents. The expression 'processing steps' thereby can refer to physically executed processing steps such as centrifugation, aliquotation, sample analysis and the like. The term 'laboratory instrument' can cover pre-analytical instruments, post-analytical instruments and also analytical instruments.

The term "vessel" as used herein can refer to any type of container suitable to store a sample or reagent in the field of analytics and more particularly, medical analytics. Such vessels can usually be designed as tubes.

The term "magazine" as used herein can basically refer to any device configured to hold a plurality of vessels and to be supplied to a laboratory instrument.

The term "path" as used herein can be any path configured similar to a ball path as it has to guide a rolling element.

The term "rolling element" as used herein can be any element that can be configured to roll such as a ball, a roller, cylinder or the like.

The term "below" as used herein can refer to an orientation with respect to a direction of gravity with the prerequisite that the drawer assembly can be in its target orientation.

With the configuration described before, the drawer can be pulled out. The rolling element can act similar to a rolling bearing in the pull-out direction, whereas the tapered first portion can prevent a movement of the drawer back in the counter-direction unless completely pulled out. Thus, a rather simple mechanism can prevent a movement of the drawer rearwards if not completely pulled out.

The first portion and the second portion may be connectable to one another by first and second connection portions at respective ends thereof. The first connection portion can be exposed to the first portion and the second portion exclusively when the drawer is in the extended position. The second connection portion can be exposed to the first portion and the second portion exclusively when the drawer is in the retracted position. Thus, the first portion and the second portion can be connected to one another when the drawer is in its end positions, either completely pulled out or completely inserted.

The lifting mechanism may be arranged at the second connection portion. Thus, the lifting mechanism can serve to move the rolling element from the second portion to the first portion when the drawer is completely inserted.

The lifting mechanism may be operable by the drawer. Thus, no further device may be provided in order to operate the lifting mechanism and to move the rolling element from the second portion to the first portion.

The lifting mechanism may comprise a lever and a tilting element. The tilting element can be tiltable by actuation of the lever between a lower position, in which the tilting element faces the second portion, and an upper position, in which the tilting element faces the first portion. Thus, the tilting mechanism can be configured to move the rolling element from the second portion to the first portion by a tilting or pivoting movement which can allow the tilting mechanism to be designed rather compact.

The lever may be configured to be actuated by engagement with the drawer. Thus, only the drawer may be needed to operate the lever which can reduce the number of constructional members.

The drawer may comprise two stopper surfaces facing one another. The lever can be located between the two stopper surfaces. Thus, the lever may be reliably operated by engagement with the stopper surfaces.

The path can be located below the drawer. Thus, the drawer assembly may be designed rather compactly.

The path may be located closer to the second end than to the first end. Thus, the path may be arranged closer to the pulled-out position of the drawer.

The path may be located adjacent the second end. Thus, the path may be easily accessible to maintenance or similar purposes.

The rolling element may a ball. Thus, the rolling element may be rather compact and roll in all directions.

The drawer assembly may further comprise a stopper element configured to prevent a movement of the drawer from the extended position to the retracted position if a magazine including at least one vessel is loaded in the drawer. Thus, loading of a magazine with still one or more vessel in it can be prevented mechanically and the magazine needs to be completely empty for re-loading of drawer.

The stopper element may be arranged at a position so as to extend across a top surface of the magazine. Thus, the stopper element may reliably detect if a vessel protrudes from the top surface of the magazine.

The stopper element may comprise at least one flap pivotable between a closed position, in which the flap extends across the top surface of the magazine in a direction substantially perpendicular to the longitudinal direction, and an open position, in which the flap exposes the top surface of the magazine. Thus, the stopper element can be configured to prevent a re-loading or inserting of the drawer if one or more vessels are in it as the stopper element may not be moved further than a position in which it extends substantially perpendicular to the longitudinal direction. Thus, the stopper element can act similar to a one-way valve.

The stopper element may comprise two flaps, each of which can be pivotable between a closed position, in which the flap extends across the top surface of the magazine in a direction substantially perpendicular to the longitudinal direction, and an open position, in which the flap exposes the top surface of the magazine. Thus, the stopper element can be configured to prevent a re-loading or inserting of the drawer if one or more vessels are in it as the stopper element may not be moved further than a position in which it extends substantially perpendicular to the longitudinal direction. Thus, the stopper element can act similar to a one-way valve.

The two flaps may face one another in the closed position. Thus, the flaps can be arranged adjacent to one another in the closed position such that the magazine may not be moved rearwards if a vessel is in it.

The drawer assembly may further comprise at least on positioning element configured to position the magazine at a target position in the drawer. Thus, a correct arrangement of the magazine can be ensured.

The positioning element may be a positioning spring or positioning clamp. Thus, a rather simple construction can correctly position the magazine.

The drawer assembly may further comprise a locking mechanism configured to lock the drawer in the retracted position. Thus, an unintended or misusing pulling out of the drawer can be prevented.

The drawer assembly may further comprise a sensor configured to detect the status of the drawer and/or the magazine. Thus, an additional safety device may be provided which can detect whether the magazine is loaded with one or more vessels and/or whether the drawer is inserted or pulled-out.

The laboratory instrument may be a laboratory storage and retrieval system or may be part of a laboratory storage and retrieval system. Thus, the disclosed drawer assembly may be used with an automated sample handling apparatus.

The disclosed laboratory instrument can comprise at least one drawer assembly as described before. Thus, the drawer assembly as described before may be used in combination with further drawer assemblies which may be independent operated from one another.

The laboratory instrument may be configured to handle a plurality of vessels for liquids. Thus, a high degree of automation may be realized.

The laboratory instrument may further comprise at least one magazine. Thus, a broad handling of many magazines may be realized.

The magazine may be a rack and the vessels for liquids may be sample tubes. Thus, common laboratory utensils may be used within the disclosed laboratory instrument.

The present disclosure can further disclose and propose a computer program including computer-executable instructions for performing the method according to the present disclosure in one or more of the embodiments enclosed herein when the program is executed on a computer or computer network. Specifically, the computer program may be stored on a computer-readable data carrier. Thus, specifically, one, more than one or even all of method steps may be performed by using a computer or a computer network, preferably by using a computer program.

The present disclosure can further disclose and propose a computer program product having program code, in order to perform the method according to the present disclosure in one or more of the embodiments enclosed herein when the program is executed on a computer or computer network. Specifically, the program code may be stored on a computer-readable data carrier.

Further, the present disclosure can disclose and propose a data carrier having a data structure stored thereon, which, after loading into a computer or computer network, such as into a working memory or main memory of the computer or computer network, may execute the method according to one or more of the embodiments disclosed herein.

The present disclosure can further propose and disclose a computer program product with program code stored on a machine-readable carrier, in order to perform the method according to one or more of the embodiments disclosed herein, when the program is executed on a computer or computer network. As used herein, a computer program product can refer to the program as a tradable product. The product may generally exist in an arbitrary format, such as in a paper format, or on a computer-readable data carrier. Specifically, the computer program product may be distributed over a data network.

Finally, the present disclosure can propose and disclose a modulated data signal which can contain instructions readable by a computer system or computer network, for performing the method according to one or more of the embodiments disclosed herein.

Referring to the computer-implemented aspects of the present disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the present present disclosure can further disclose:

A computer or computer network comprising at least one processor, wherein the processor can be adapted to perform the method according to one of the embodiments described in this description, a computer loadable data structure that can be adapted to perform the method according to one of the embodiments described in this description while the data structure is being executed on a computer, a computer program, wherein the computer program can be adapted to perform the method according to one of the embodiments described in this description while the program is being executed on a computer, a computer program comprising a program for performing the method according to one of the embodiments described in this description while the computer program is being executed on a computer or on a computer network, a computer program comprising a program according to the preceding embodiment, wherein the program is stored on a storage medium readable to a computer, a storage medium, wherein a data structure can be stored on the storage medium and wherein the data structure can be adapted to perform the method according to one of the embodiments described in this description after having been loaded into a main and/or working storage of a computer or of a computer network, and a computer program product having program code, wherein the program code can be stored or are stored on a storage medium, for performing the method according to one of the embodiments described in this description, if the program code is executed on a computer or on a computer network.

A drawer assembly for a laboratory instrument can comprise a drawer configured to be loaded with a magazine for receiving vessels for liquids such as, for example, sample tubes, of the laboratory instrument. The drawer can comprise a front end and a rear end. The drawer assembly can also comprise a frame comprising at least one portion arranged adjacent the drawer. The portion can extend in a longitudinal direction from a first end to a second end. The drawer can be moveable relative to the frame between a retracted position, in which the drawer is retracted in the frame and the front end is adjacent the first end, and an extended position, in which the drawer is extended from the frame and the front end is adjacent the second end. The frame can comprise a path having a first portion and a second portion below the first portion. The first portion and the second portion can extend in a direction parallel to the longitudinal direction. The first portion can be tapered towards the first end and facing the drawer. The drawer assembly can also comprise a rolling element moveable in the path and a lifting mechanism configured to lift the rolling element from the second portion to the first portion when the drawer is in the retracted position. The path can be configured such that the rolling element can be located in the first portion and can contact the drawer when the drawer is moved from the retracted position to the extended position and that the rolling element can be allowed to enter the second portion exclusively when the drawer is in the extended position.

The first portion and the second portion can be connectable to one another by first and second connection portions at respective ends thereof. The first connection portion can be exposed to the first portion and the second portion exclusively when the drawer is in the extended position. The second connection portion can be exposed to the first portion and the second portion exclusively when the drawer is in the retracted position.

The lifting mechanism can be arranged at the second connection portion. The lifting mechanism can be operable by the drawer. The lifting mechanism can comprise a lever and a tilting element. The tilting element can be tiltable by actuation of the lever between a lower position, in which the tilting element faces the second portion, and an upper position, in which the tilting element faces the first portion. The lever can be configured to be actuated by engagement with the drawer. The drawer can comprise two stopper surfaces facing one another. The lever can be located between the two stopper surfaces.

The path can be located below the drawer. The path can be located closer to the second end than to the first end. The path can be located adjacent the second end.

The rolling element can be a ball.

The drawer assembly can further comprise a stopper element configured to prevent a movement of the drawer from the extended position to the retracted position if a magazine including at least one vessel is loaded in the drawer. The stopper element can be arranged at a position so as to extend across a top surface of the magazine.

The stopper element can comprise at least one flap pivotable between a closed position, in which the flap can extend across the top surface of the magazine in a direction substantially perpendicular to the longitudinal direction, and an open position, in which the flap can expose the top surface of the magazine.

The stopper element can comprise two flaps, each of which can be pivotable between a closed position, in which the flap can extend across the top surface of the magazine in a direction substantially perpendicular to the longitudinal direction, and an open position, in which the flap can expose the top surface of the magazine. The two flaps can face one another in the closed position.

The drawer assembly can further comprise at least on positioning element configured to position the magazine at a target position in the drawer. The positioning element can be a positioning spring or positioning clamp.

The drawer assembly can further comprise a locking mechanism configured to lock the drawer in the retracted position.

The drawer assembly can further comprise a sensor configured to detect the status of the drawer and/or the magazine.

The laboratory instrument can be a laboratory storage and retrieval system or can be part of a laboratory storage and retrieval system.

A laboratory instrument comprising at least one drawer assembly according to any of the above embodiments is presented. The laboratory instrument can be configured to handle a plurality of vessels for liquids. The laboratory instrument can further comprise at least one magazine. The magazine can be a rack and the vessels for liquids can be sample tubes.

Figure 2:
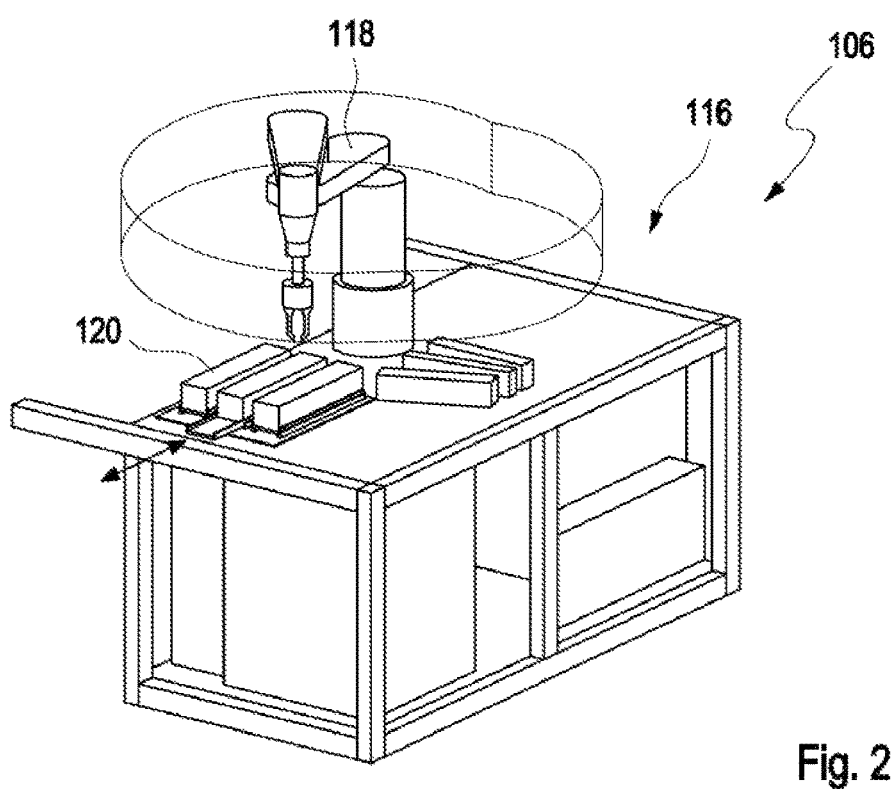
FIG. 2 illustrates a perspective view of a rack handler area according to an embodiment of the present disclosure.
Figure 3:
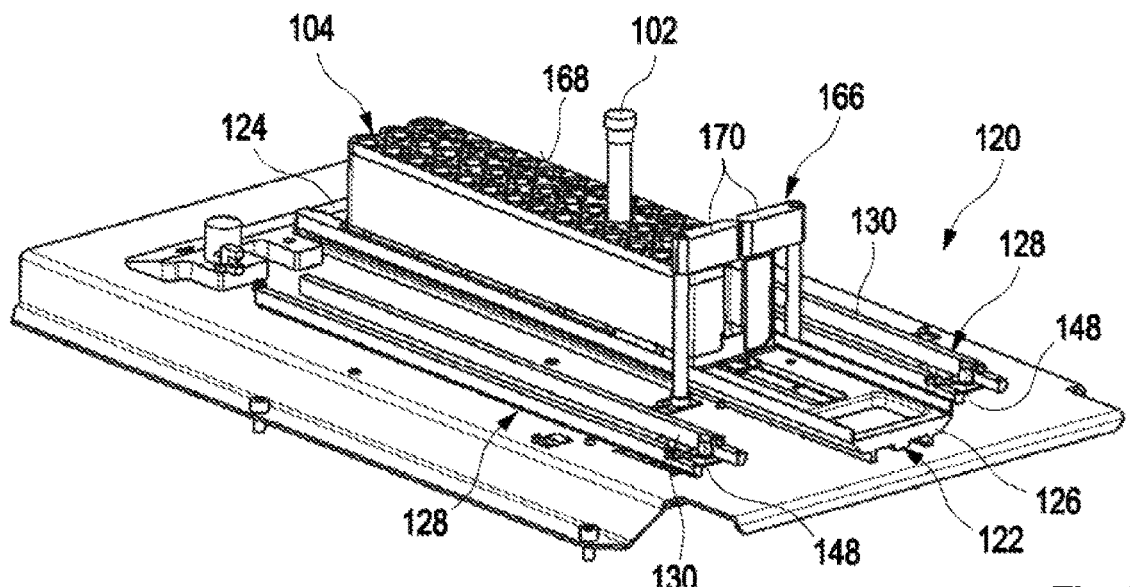
FIG. 3 illustrates a perspective view of the drawer assembly according to an embodiment of the present disclosure.

Referring initially to FIG. 1, FIG. 1 shows a perspective view of a laboratory instrument 100. The laboratory instrument 100 can be a so-called laboratory storage and retrieval system. Alternatively, the laboratory instrument 100 may be part of a laboratory storage and retrieval system. The laboratory instrument 100 can be configured to handle a plurality of vessels 102 (FIG. 3) for liquids. The vessels 102 for liquids can be sample tubes in this embodiment. The laboratory instrument 100 can further comprise at least one magazine 104 (FIGS. 2 and 3). The magazine 104 can be configured to receive the vessels 102. The magazine 104 can be a rack.

The laboratory instrument 100 can comprise a rack handler section 106 and a storage section 108. Between the two sections 106, 108, a loading/unloading interface (not shown in detail) can be provided through which racks can be transferred from the rack handler section 106 into the storage section 108 and back (in case of retrieval). This loading/unloading interface may include a gate or the like.

The storage section 108 may comprise a refrigerator 110. A storage section in the context of the present disclosure can be a cabinet of various sizes which is able to store a plurality of sample tubes in magazines 104. The storage section may have a tempering unit to hold the ambient temperature for the tubes within the storage section below room temperature, possibly below about 18° C. and possibly below about 10° C.

In its inside, the storage section 108 can comprise a plurality of shelves for storage of a high number of magazines 104. All vessels 102 contained in magazines 104 (i.e. incoming racks of various types) fulfilling the geometry criteria of the present disclosure can be taken out of their respective magazines 104 and can be re-sorted in suitable storage racks before being loaded into the storage section 108. The storage section may be large enough for one or two human beings to enter the inside of the storage section 108 through a door (not shown in detail). In case the door is opened, a safety switching circuit can ensure that all moving systems (like robotic arms or other transfer or conveying systems) come to a standstill, for example in a neutral or home position. The magazines 104 can be multi-row racks, e.g. three rows with more than ten positions, for example 13 to 108 positions. Further, the storage section 108 may comprise a disposal unit 112. The disposal unit 112 can be connected with the storage section 108 via an internal opening (not shown in detail) in a wall separating the storage section 108 from the disposal unit 112. Through this opening, vessels 102 whose expiration date (i.e., shelf life) has elapsed can be disposed automatically in the disposal unit 112. The rack handler section 106 can have a housing consisting of several outer walls with windows so that operating personal can have a direct visual overview of the rack handler's functioning. The rack handler section 106 can comprise an opening 114 in one of the outer walls through which racks can be inserted into the laboratory instrument 100.

FIG. 2 shows a perspective view of a rack handler area 116 of the rack handler section 106. The opening 114 can lead to the rack handler area 116 which can comprise at least one robotic arm 118. The opening 114 may be closed by a sliding or retractable door (not shown in detail).

The laboratory instrument 100 can further comprise at least one drawer assembly 120. The drawer assembly 120 can be located in the rack handler section 106. By the drawer assembly 120, emptied magazines 104 and/or magazines 104 containing vessels 102 with error designations and/or magazines 104 containing at least one retrieved vessels 102 can be taken out of the laboratory instrument 100. Hereinafter, the drawer assembly 120 will be described in further detail.

FIG. 3 shows a perspective view of the drawer assembly 120. It can be noted that more than one drawer assembly 120 may be present even though the following explanations are made only with respect to one drawer assembly 120. The drawer assembly 120 can comprise a drawer 122 configured to be loaded with a magazine 104 for receiving vessels 102 for liquids such as, for example, sample tubes, of the laboratory instrument 100. The drawer can comprise a front end 124 and a rear end 126. The front end 124 and the rear end 126 can be located opposite to one another. The front end 124 can be configured to be the end of the drawer 122 facing the laboratory instrument 100. The rear end 126 can be configured to be the end of the drawer 122 facing away from the laboratory instrument 100 and to be exposed or accessible to a user of the laboratory instrument 100. The drawer assembly 120 can further comprise a frame 128 comprising at least one portion 130 arranged adjacent the drawer 122.

Figure 4:
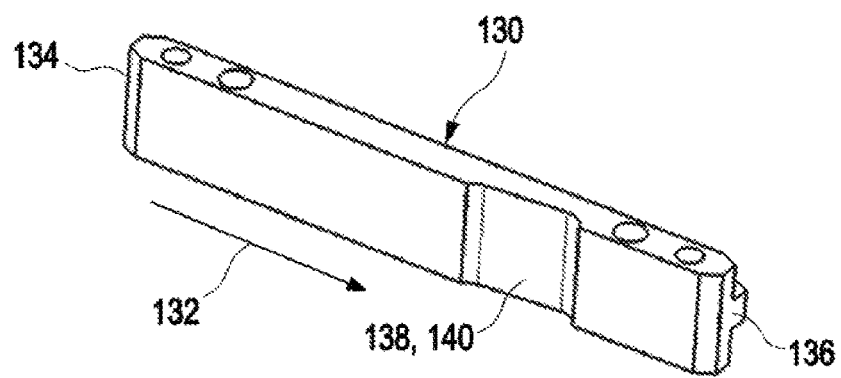
FIG. 4 illustrates a perspective view of the portion according to an embodiment of the present disclosure.

FIG. 4 shows a perspective view of the portion 130. The portion 130 can extend in a longitudinal direction 132 from a first end 134 to a second end 136. The drawer 122 can be connected to the frame 128. The drawer 122 can be moveable relative to the frame 128 between a retracted position, in which the drawer 122 is retracted or inserted in the frame 128 and the front end 124 is adjacent the first end 134, and an extended position, in which the drawer 122 is extended from the frame 128 and the front end 124 is adjacent the second end 136. The frame 128 can comprise a path 138.

Figure 5:
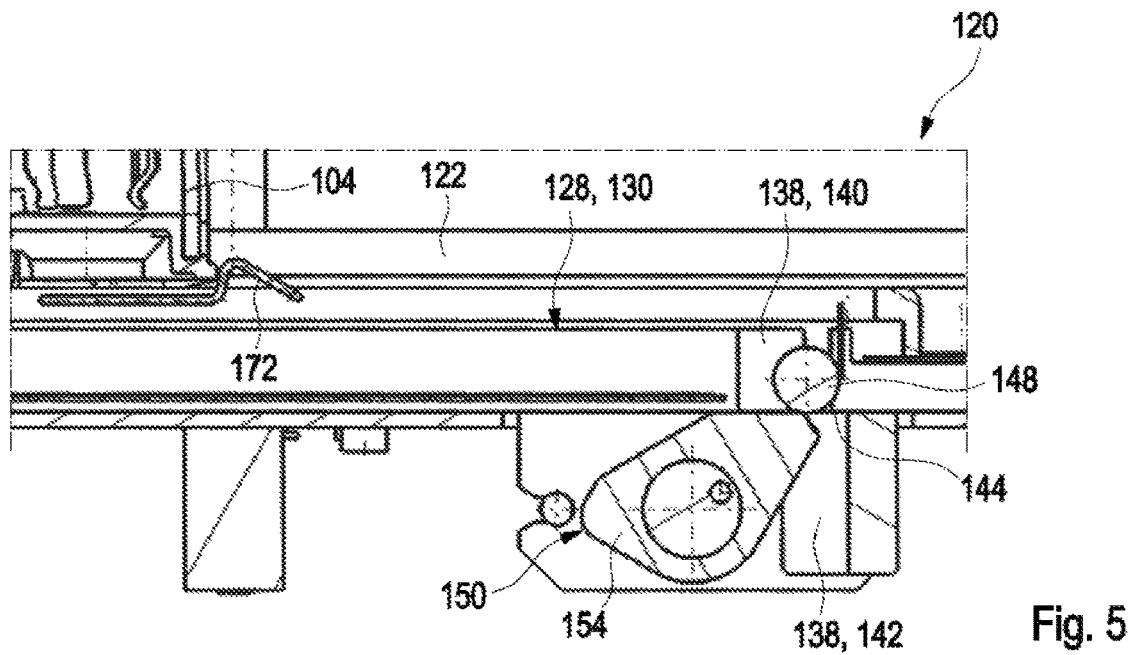
FIG. 5 illustrates a cross-sectional view of the drawer assembly according to an embodiment of the present disclosure.
Figure 6:
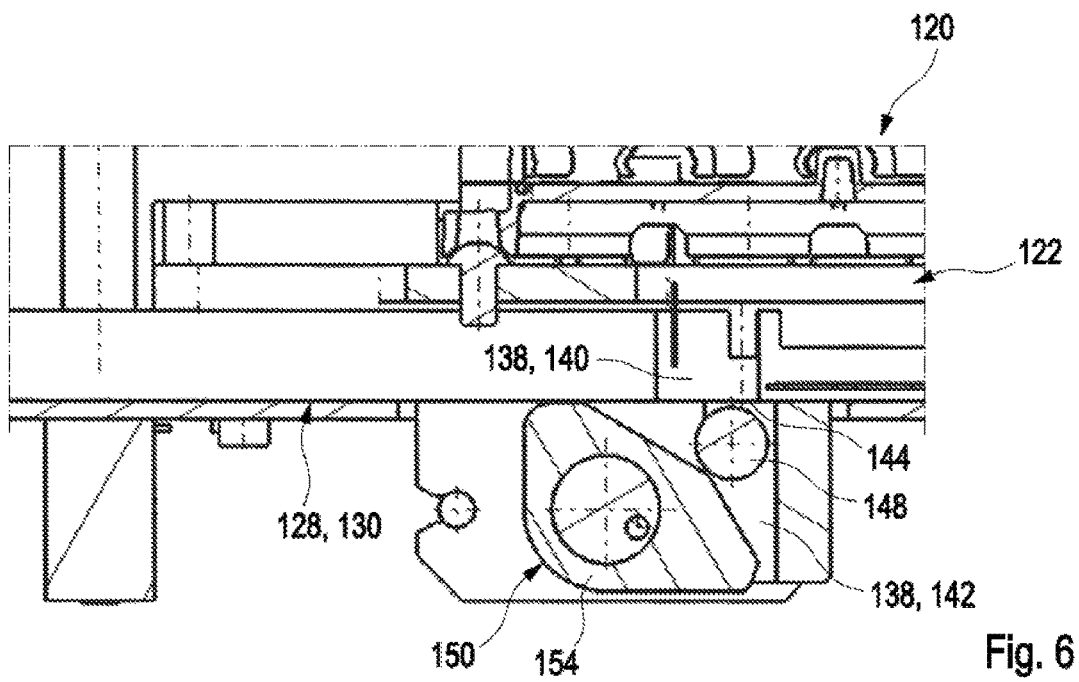
FIG. 6 illustrates another cross-sectional view of the drawer assembly according to an embodiment of the present disclosure.
Figure 7:
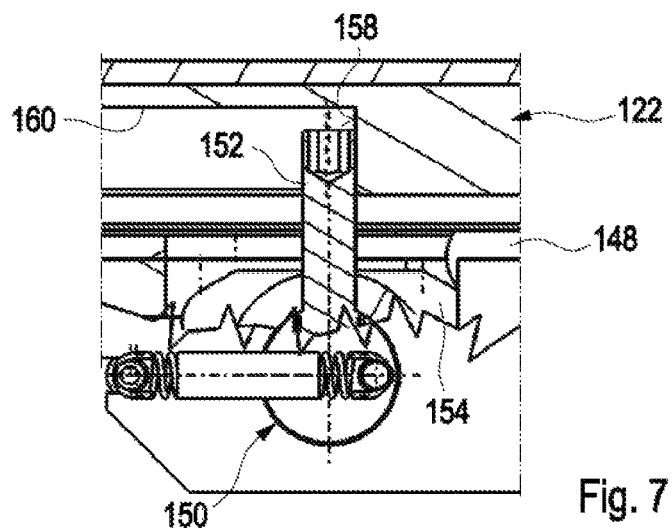
FIG. 7 illustrates yet another cross-sectional view of the drawer assembly according to an embodiment of the present disclosure.
Figure 8:
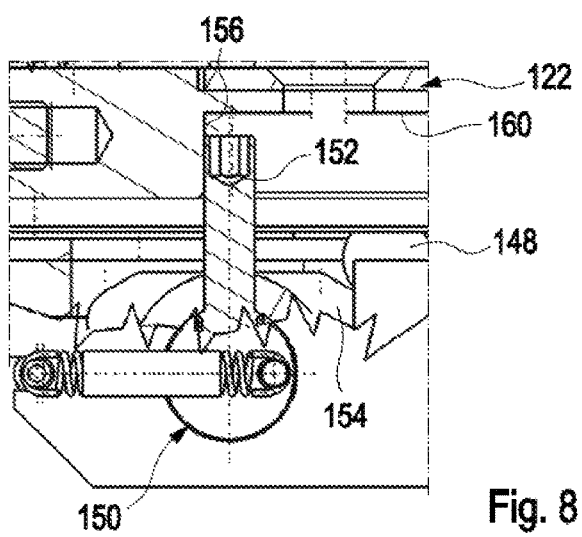
FIG. 8 illustrates still yet another cross-sectional view of the drawer assembly according to an embodiment of the present disclosure.

FIGS. 5 and 6 show cross-sectional views of the drawer assembly 120 in different operation states. FIGS. 7 and 8 show cross-sectional views of the drawer assembly 120 along planes parallel to the ones on FIGS. 5 and 6 in the different operation states. The path 138 can be located below the drawer 122. The path 138 can be located closer to the second end 136 than to the first end 134. More particularly, the path 138 can be located adjacent the second end 136. The path can have a first portion 140 and a second portion 142 below the first portion 140. The first portion 140 and the second portion 142 can extend in a direction substantially parallel to the longitudinal direction 132. The first portion 140 can be tapered towards the first end 134 and can face the drawer 122. The first portion 140 and the second portion 142 can be connectable to one another by first and second connection portions 144, 146 at respective ends thereof. The first connection portion 144 can be exposed to the first portion 140 and the second portion 142 exclusively when the drawer 122 is in the extended position. The second connection portion 146 can be exposed to the first portion 140 and the second portion 142 exclusively when the drawer 122 is in the retracted position.

The drawer assembly 120 can further comprise a rolling element 148 moveable in the path 138. In one embodiment, the rolling element 148 can be a ball. The path 138 can be designed or configured such that the rolling element 148 can be located in the first portion 140 and can contact the drawer 122 when the drawer 122 is moved from the retracted position to the extended position as shown in FIG. 5 and that the rolling element 148 can be allowed to enter the second portion 142 exclusively when the drawer 122 is in the extended position as shown in FIG. 6 and as will be explained in further detail below.

The drawer assembly 120 can further comprise a lifting mechanism 150 configured to lift the rolling element 148 from the second portion 142 to the first portion 140 when the drawer is in the retracted position. The lifting mechanism 150 can be arranged at the second connection portion. The lifting mechanism 150 can be operable by the drawer. The lifting mechanism 150 can comprise a lever 152 and a tilting element 154. The tilting element 154 can be tiltable by actuation of the lever 152 between a lower position shown in FIG. 6, in which the tilting element 154 faces the second portion 142, and an upper position shown in FIG. 5, in which the tilting element 154 faces the first portion 140. The lever 152 can be configured to be actuated by engagement with the drawer 122. For this purpose, the drawer 122 can comprise two stopper surfaces 156, 158 facing one another, wherein the lever 152 can be located between the two stopper surfaces 156, 158. The stopper surfaces 156, 158 can be located at a lower side 160 of the drawer 122. The first stopper surface 156 can be arranged adjacent the front end 124 and the second stopper surface 158 can be arranged adjacent the rear end 126. FIG. 7 shows the lever 152 engaged by the second stopper surface 158, which can mean that the tilting element 154 is in the upper position. FIG. 8 shows the lever 152 engaged by the first stopper surface 156, which can mean that the tilting element 154 is in the lower position.

FIGS. 9 and 10 show plan views of the portion 130 in different operation states of the drawer assembly 120. As the first portion 140 is tapered towards the first end 134, the drawer 122 can be allowed to move only towards the extended position as the rolling element 148 present in the first portion 140 may only be moved in the direction indicated by arrow 162 in FIG. 9. A movement of the drawer 122 in the opposite direction towards the retracted position can be prevented by the rolling element 148 as the rolling element 148 may only be moved in the counter-direction within the first portion 140 to a rather small degree in the direction indicated by arrow 164 in FIG. 10.

FIGS. 11 and 12 show perspective views of the drawer assembly 120. The drawer assembly 120 can further comprise a stopper element 166 configured to prevent a movement of the drawer 122 from the extended position to the retracted position if a magazine 104 including at least one vessel 102 is loaded in the drawer 122. The stopper element 166 can be arranged at a position so as to extend across a top surface 168 of the magazine 104. The stopper element 166 can comprise at least one flap 170 pivotable between a closed position shown in FIG. 11, in which the flap 170 can extend across the top surface 168 of the magazine 104 in a direction substantially perpendicular to the longitudinal direction 132, and an open position shown in FIG. 12, in which the flap 170 can expose the top surface 168 of the magazine 104. In one embodiment, the stopper element 166 can comprise two flaps 170, each of which can be pivotable between a closed position, in which each of the flaps 170 extends across the top surface 168 of the magazine 104 in a direction substantially perpendicular to the longitudinal direction 132, and an open position, in which each of the flaps 170 can expose the top surface 168 of the magazine 104. If the drawer 122 is completely in the retracted position, the flaps 122 do not extend across the top surface 168 of the magazine 104. Rather, the flaps 170 can extend in a direction substantially perpendicular to the longitudinal direction 132 and adjacent the top surface 168. The two flaps 170 face one another in the closed position. In the open position, the flaps 170 can extend substantially parallel to one another and in a direction substantially parallel to the longitudinal direction 132 towards the second end 136 of the portion 130 of the frame 128. It can be noted that FIG. 12 shows a state where the drawer 122 is pull out whereas FIG. 11 shows a state where the drawer 122 is inserted or loaded in the frame 128.

The drawer assembly 120 can further comprise at least on positioning element 172 configured to position the magazine 104 at a target position in the drawer 122. In one embodiment, the positioning element 172 can be a positioning spring or positioning clamp.

The drawer assembly 120 may optionally further comprise a locking mechanism configured to lock the drawer 122 in the retracted position. The drawer assembly 120 may optionally further comprise a sensor configured to detect the status of the drawer 122 and/or the magazine 104. For example, the sensor may detect whether the drawer 122 is in the retracted or extended position or any position therebetween. In addition, or alternatively, the sensor may detect whether the magazine 104 is emptied or whether at least one vessel is present.

Figure 13:
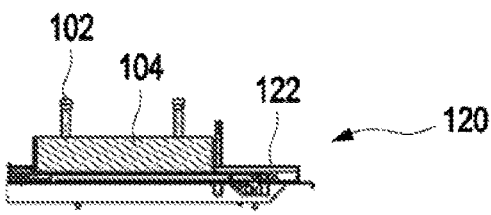
FIGS. 13A-D illustrate different cross-sectional views of the drawer assembly in a first operation state according to an embodiment of the present disclosure.
Figure 13:
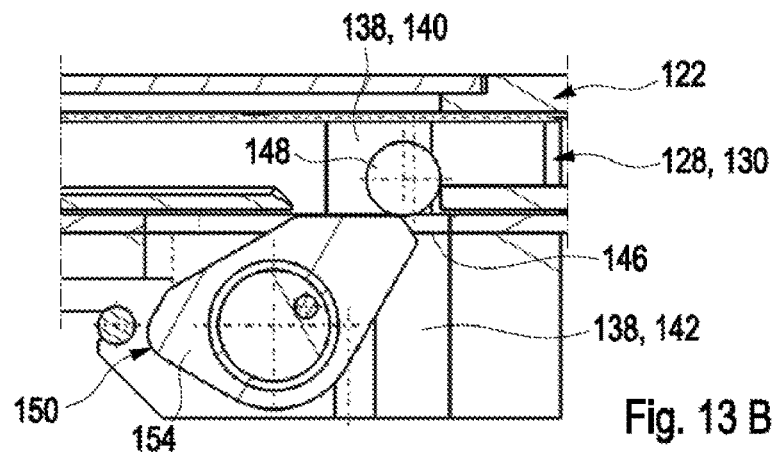
Figure 13:
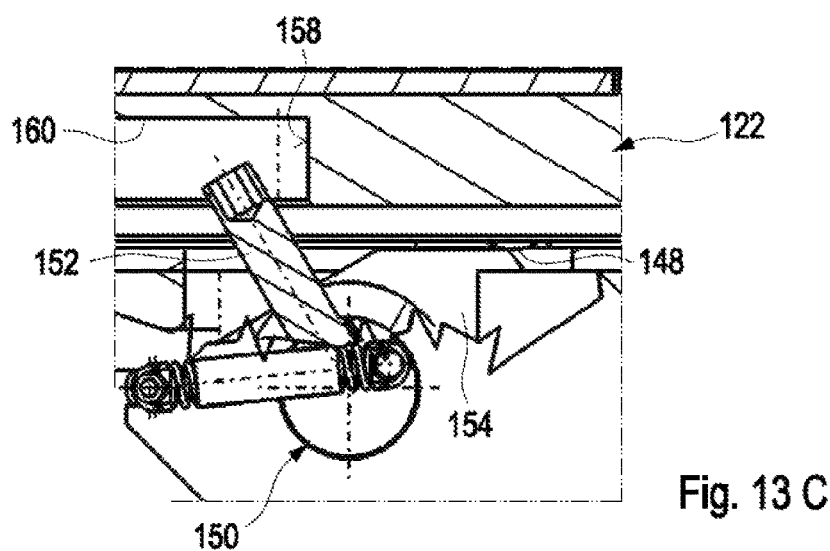
Figure 13:
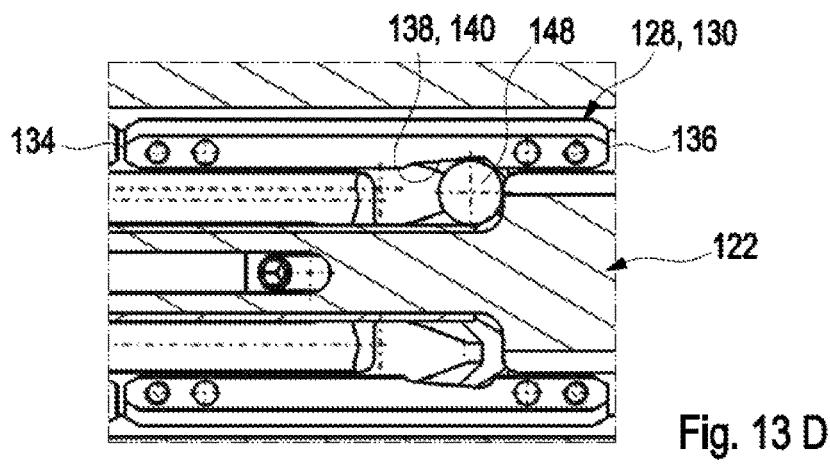

FIGS. 13A-D show different cross-sectional views of the drawer assembly 120 in a first operation state. In the first operation state, shown in FIGS. 13A-D, the drawer 122 can be in the retracted position as particularly shown in FIG. 13A. The tilting element 154 of the lifting mechanism 150 can be in the upper position as shown in FIG. 13B, in which the tilting element 154 can face the first portion 140. The rolling element 148 can be in the first portion 140 as shown in FIGS. 13B and 13D. The lever 152 of the lifting mechanism 150 can be engaged by the second stopper surface 158 of the drawer 122 as shown in FIG. 13C.

Figure 14:
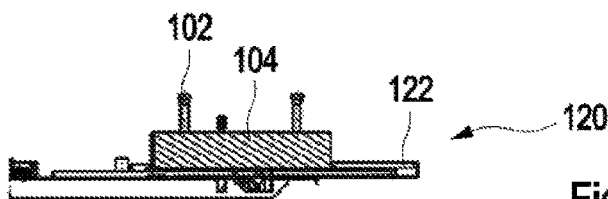
FIGS. 14A-D illustrate different cross-sectional views of the drawer assembly in a second operation state according to an embodiment of the present disclosure.
Figure 14:
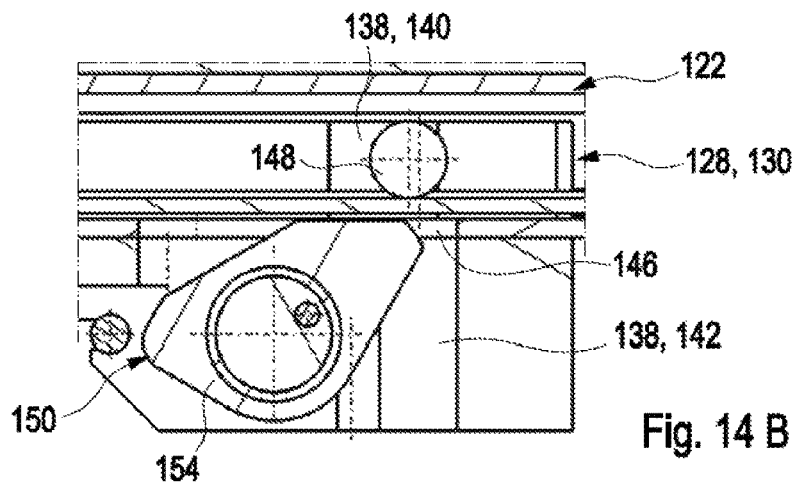
Figure 14:
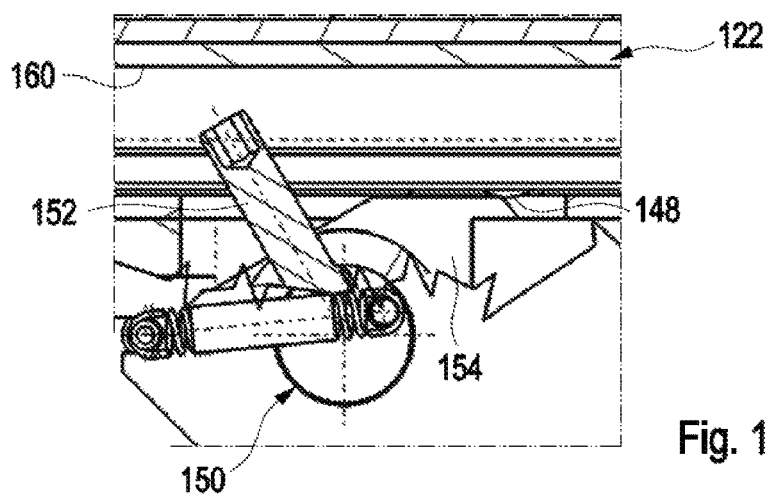
Figure 14:
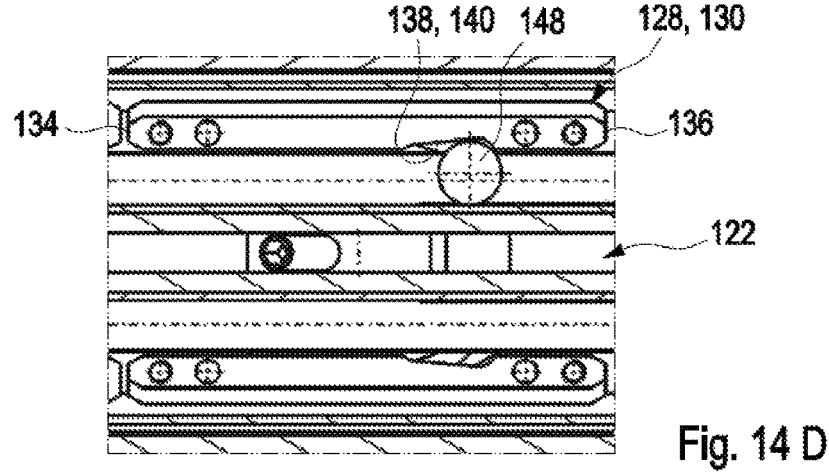

FIGS. 14A-14D show different cross-sectional views of the drawer assembly 120 in a second operation state. In the second operation state shown in FIGS. 14A-14D, the drawer 122 is in an intermediate position on the way from the retracted position to the extended position as particularly shown in FIG. 14A. In other words, the drawer 122 has started to be pulled out by a user such that the drawer is located right if compared to the retracted position shown in FIG. 13A. The tilting element 154 of the lifting mechanism 150 is still in the upper position as shown in FIG. 14B, in which the tilting element 154 faces the first portion 140. The rolling element 148 is still in the first portion 140 as shown in FIGS. 14B and 14D. The lever 152 of the lifting mechanism 150 has not been moved and is no longer engaged by the second stopper surface 158 of the drawer 122 but is located between the first and second stopper surfaces 156, 158 as shown in FIG. 14C. The tapered first portion 140 and the rolling element 148 obstruct the drawer 122 from moving leftwards with respect to the illustration of FIG. 14D.

Figure 15:
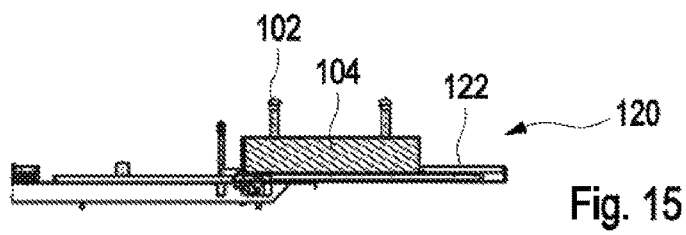
FIGS. 15A-D illustrate different cross-sectional views of the drawer assembly in a third operation state according to an embodiment of the present disclosure.
Figure 15:
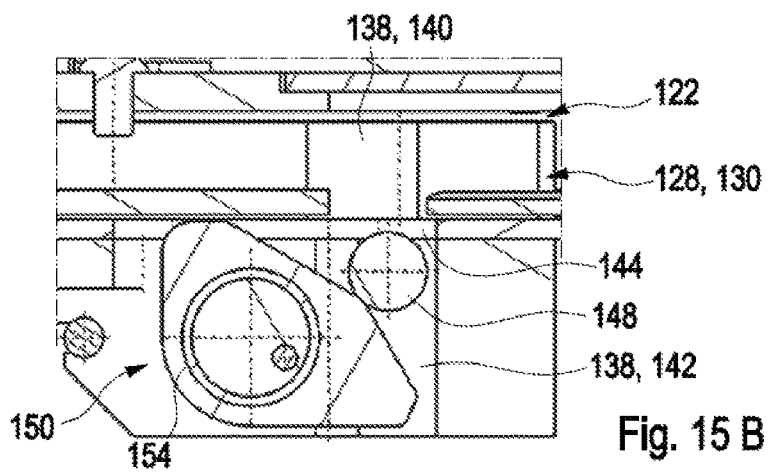
Figure 15:
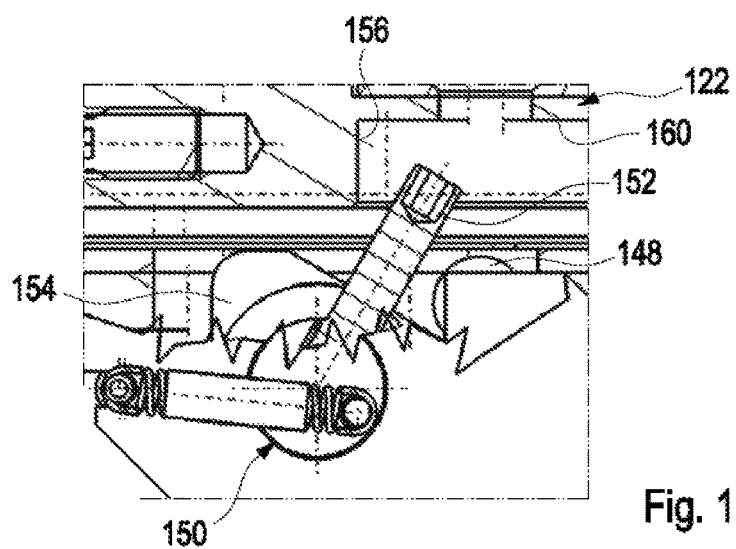
Figure 15:
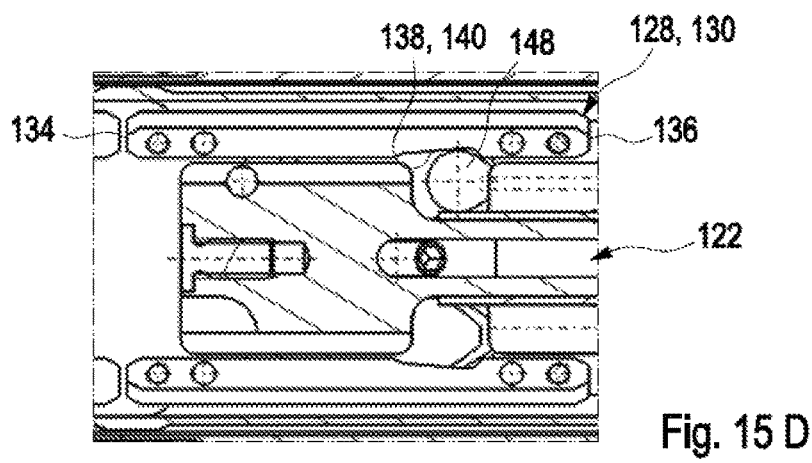

FIGS. 15A-15D show different cross-sectional views of the drawer assembly 120 in a third operation state. In the third operation state shown in FIGS. 15A-15D, the drawer 122 is in the extended position as particularly shown in FIG. 15A. In other words, the drawer 122 has been completely pulled out by the user such that the drawer is located right if compared to the intermediate position shown in FIG. 14A. The tilting element 154 of the lifting mechanism 150 is in the lower position as shown in FIG. 15B, in which the tilting element 154 faces the second portion 142. The rolling element 148 is allowed to enter the second portion 142 through the first connection portion 144 as shown in FIGS. 15B and 15D. The lever 152 of the lifting mechanism 150 is engaged by the first stopper surface 156 of the drawer 122 as shown in FIG. 15C.

Figure 16:
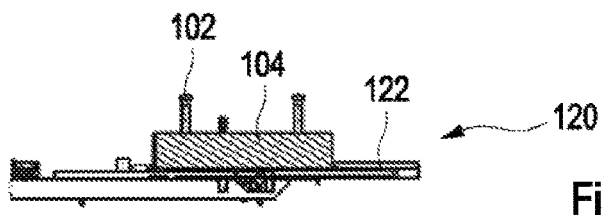
FIGS. 16A-D illustrate different cross-sectional views of the drawer assembly in a fourth operation state according to an embodiment of the present disclosure.
Figure 16:
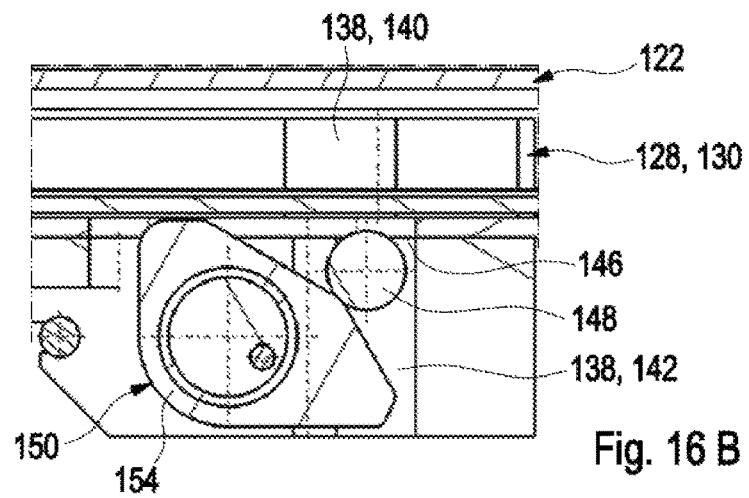
Figure 16:
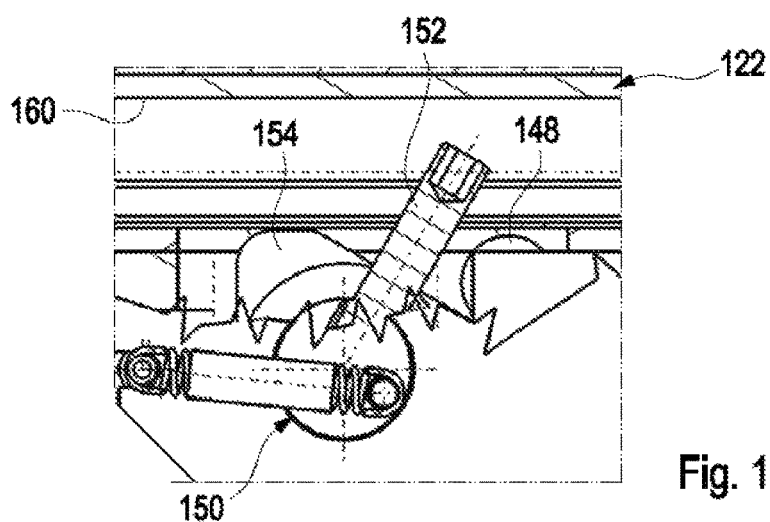
Figure 16:
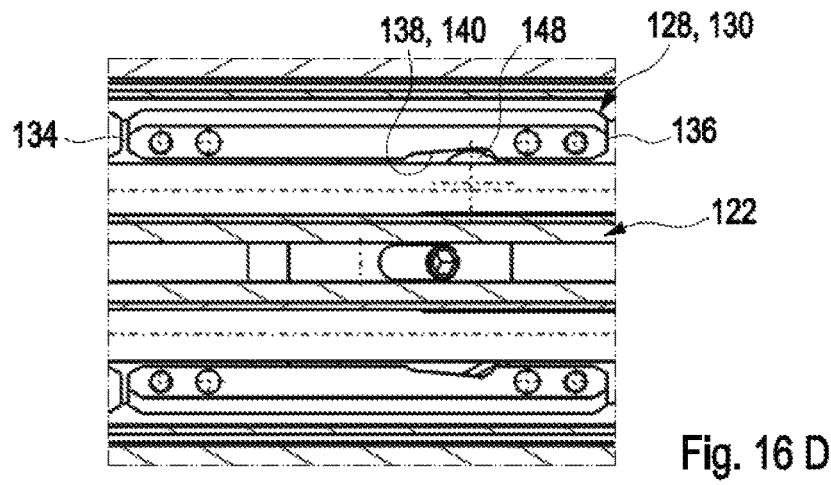

FIGS. 16A-16D show different cross-sectional views of the drawer assembly 120 in a fourth operation state. In the fourth operation state shown in FIGS. 16A-16D, the drawer 122 is in an intermediate position on the way from the extended position to the retracted position as particularly shown in FIG. 16A. In other words, the drawer 122 has started to be loaded into the laboratory instrument 100 by a user such that the drawer is located left if compared to the extended position shown in FIG. 15A. The tilting element 154 of the lifting mechanism 150 is still in the lower position as shown in FIG. 16B, in which the tilting element 154 faces the second portion 142. The rolling element 148 is still in the second portion 142 as shown in FIGS. 16B and 16D. The lever 152 of the lifting mechanism 150 has not been moved and is no longer engaged by the first stopper surface 156 of the drawer 122 but is located between the first and second stopper surfaces 156, 158 as shown in FIG. 16C. As the second portion 142 is not tapered but may be designed straight or the like, the rolling element 148 does not obstruct the drawer 122 from moving leftwards with respect to the illustration of FIG. 16D.

When the drawer 122 is moved further leftwards with respect to the illustrations of FIGS. 16A and 16D, the drawer 122 is moved into the retracted position again. The tilting element 154 of the lifting mechanism 150 is moved from the lower position to the upper position when the lever 152 of the lifting mechanism 150 is engaged by the second stopper surface 158 of the drawer 122. Thereby, the rolling element 148 is moved by the tilting element 154 upwards into the first portion 140 through the second connection portion 146. Thus, the drawer 122 is positioned again as shown in FIG. 13A. In this position, the positioning element 172 positions the magazine 104 at its target position in the drawer 122 by a biasing force in a predetermined direction.

If at least one vessel 102 is present in the magazine 104 while the drawer 122 is in the retracted position, the flaps 170 of the stopper element 166 can be in the closed position and can extend in a direction substantially perpendicular to the longitudinal direction 132. When the drawer 122 is moved to the extended position, the flaps 170 can be moved or pivoted to the open position by engaging the vessel 102 and extend substantially parallel to the longitudinal direction 132 as shown in FIG. 12. After removing all of the vessels 102, the flaps 170 may move or pivot back in the closed position and extend in a direction substantially perpendicular to the longitudinal direction 132. If not all of the vessels 102 are removed from the magazine 104 but there is still one or more vessels 102 present in the magazine 104, the magazine 104 can be blocked from moving again in the retracted position as the flaps 170 can engage the vessel(s) 102 and may not be allowed to move or pivot in the counter-direction towards the first end 134 of the portion 130 of the frame 128.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A drawer assembly for a laboratory instrument, the drawer assembly comprising:
   a drawer configured to be loaded with a magazine for receiving vessels for liquids of the laboratory instrument, wherein the drawer comprises a front end and a rear end;
   a frame comprising at least one portion arranged adjacent the drawer, wherein the portion extends in a longitudinal direction from a first end to a second end, wherein the drawer is moveable relative to the frame between a retracted position, in which the drawer is retracted in the frame and the front end is adjacent the first end, and an extended position, in which the drawer is extended from the frame and the front end is adjacent the second end, wherein the frame comprises a path having a first portion and a second portion below the first portion, wherein the first portion and the second portion extend in a direction parallel to the longitudinal direction, and wherein the first portion is tapered towards the first end and facing the drawer;

a rolling element moveable in the path;

a lifting mechanism configured to lift the rolling element from the second portion to the first portion when the drawer is in the retracted position, wherein the path is configured such that the rolling element is located in the first portion and contacts the drawer when the drawer is moved from the retracted position to the extended position and that the rolling element is allowed to enter the second portion exclusively when the drawer is in the extended position; and a stopper element configured to prevent movement of the drawer from the extended position to the retracted position when the magazine loaded with at least one vessel is in the drawer, wherein the stopper element is arranged at a position so as to extend across a top surface of the magazine.

2. The drawer assembly according to claim 1, wherein the first portion and the second portion are connectable to one another by a first connection portion at one end of the first portion and a second connection portion at one ends of the second portion, wherein the first connection portion is exposed to the first portion and the second portion exclusively when the drawer is in the extended position, and wherein the second connection portion is exposed to the first portion and the second portion exclusively when the drawer is in the retracted position.

3. The drawer assembly according to claim 1, wherein the lifting mechanism is operable by the drawer, wherein the lifting mechanism comprises a lever and a tilting element, wherein the tilting element is tiltable by actuation of the lever between a lower position, in which the tilting element faces the second portion, and an upper position, in which the tilting element faces the first portion.

4. The drawer assembly according to claim 3, wherein the lever is configured to be actuated by engagement with the drawer.

5. The drawer assembly according to claim 3, wherein the drawer comprises two stopper surfaces facing one another and wherein the lever is located between the two stopper surfaces.

6. The drawer assembly according to claim 1, wherein the path is located below the drawer.

7. The drawer assembly according to claim 1, wherein the path is located adjacent the second end.

8. The drawer assembly according to claim 1, wherein the stopper element comprises at least one flap pivotable between a closed position, in which the flap extends across the top surface of the magazine in a direction perpendicular to the longitudinal direction, and an open position, in which the flap exposes the top surface of the magazine.

9. The drawer assembly according to claim 8, wherein the stopper element comprises two flaps, each of which is pivotable between a closed position, in which the flap extends across the top surface of the magazine in a direction perpendicular to the longitudinal direction, and an open position, in which the flap exposes the top surface of the magazine.

10. The drawer assembly according to claim 1, further comprising, at least one positioning element configured to position the magazine at a target position in the drawer.

11. The drawer assembly according to claim 1, further comprising, a locking mechanism configured to lock the drawer in the retracted position.

12. The drawer assembly according to claim 1, further comprising, a sensor configured to detect a status of the drawer and/or the magazine.

13. The drawer assembly according to claim 1, wherein the laboratory instrument is a laboratory storage and retrieval system or is part of a laboratory storage and retrieval system.

14. The drawer assembly according to claim 1, wherein the vessels for liquids are sample tubes.

* * * * *